(12) United States Patent
Hanafusa et al.

(10) Patent No.: US 7,823,535 B2
(45) Date of Patent: Nov. 2, 2010

(54) LIQUID PORTIONING METHOD AND DEVICE

(75) Inventors: Nobuhiro Hanafusa, Kyoto (JP); Kiyohiro Sugiyama, Kyoto (JP); Masaru Furuta, Kyoto (JP); Ryo Yamaguchi, Kyoto (JP); Nobuyuki Akinaga, Kyoto (JP); Keisuke Miyamoto, Kyoto (JP); Ryuh Konoshita, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 1299 days.

(21) Appl. No.: 10/529,005

(22) PCT Filed: Sep. 29, 2003

(86) PCT No.: PCT/JP03/12447
§ 371 (c)(1),
(2), (4) Date: Jan. 13, 2006

(87) PCT Pub. No.: WO2004/036228
PCT Pub. Date: Apr. 29, 2004

(65) Prior Publication Data
US 2006/0144331 A1    Jul. 6, 2006

(30) Foreign Application Priority Data

| Sep. 27, 2002 | (JP) | ............... 2002-282513 |
| Nov. 7, 2002 | (JP) | ............... 2002-324237 |
| Nov. 11, 2002 | (JP) | ............... 2002-326681 |
| Jun. 6, 2003 | (JP) | ............... 2003-161482 |
| Jun. 6, 2003 | (JP) | ............... 2003-161483 |
| Jun. 6, 2003 | (JP) | ............... 2003-161484 |

(51) Int. Cl.
*B05C 11/10*    (2006.01)

(52) U.S. Cl. ............ 118/665; 118/676; 118/677; 118/679; 118/688; 118/712; 118/713

(58) Field of Classification Search .......... 118/665, 118/676, 677, 679, 688, 712, 713
See application file for complete search history.

(56) References Cited

U.S. PATENT DOCUMENTS 6,121,048 A    9/2000    Zaffaroni et al.
(Continued)

FOREIGN PATENT DOCUMENTS

EP    1 179 368 A2    2/2002
(Continued)

OTHER PUBLICATIONS

PCT International Search Rerpot for PCT/JP2003/12447 mailed on Jan. 27, 2004.
(Continued)

*Primary Examiner*—George R Koch, III
(74) *Attorney, Agent, or Firm*—Cheng Law Group, PLLC

(57) ABSTRACT

Methods and apparatuses for dispensing samples or reagents onto a target object are provided. A dispensing position designating section (62) designates the dispensing position on the target object (50), such as a membrane, based on an image of the target object (50) displayed on a monitoring section (60). A dispensing control section (64) positions the target object and the dispensing device relative to each other so that the designated dispensing position on the target object is placed beneath the dispensing device (10) and controls the dispensing operation of the dispensing device (10). A dispensing position information creating section (68) creates dispensing position information about the dispensing position on the target object (50) which is designated by the dispensing position designating section (62) and to which the dispensing operation has been performed and outputs it to the outside.

11 Claims, 11 Drawing Sheets

U.S. PATENT DOCUMENTS

2002/0009391 A1 1/2002 Marquiss et al.
2004/0261700 A1* 12/2004 Edwards et al. ............ 118/679

FOREIGN PATENT DOCUMENTS

| JP | 01-219535 | A1 | 9/1989 |
| JP | 03-012550 | A1 | 1/1991 |
| JP | 06-066558 | A1 | 3/1994 |
| JP | 07-333231 | A1 | 12/1995 |
| JP | 10-307088 | A1 | 11/1998 |
| JP | 11-287812 | A1 | 10/1999 |
| JP | 2001-021558 | A | 1/2001 |
| JP | 2002-162404 | A1 | 6/2002 |
| WO | WO-00/14197 | A1 | 3/2000 |
| WO | WO-01/35099 | A1 | 5/2001 |
| WO | WO-02/34944 | A1 | 5/2002 |
| WO | WO-02/052393 | A1 | 7/2002 |

OTHER PUBLICATIONS

Notification of Reasons for Refusal for the Application No. 2003-161482 from Japan Patent Office mailed Jan. 6, 2009.
Notification of Reasons for Refusal for the Application No. 2003-161484 from Japan Patent Office mailed Jan. 6, 2009.
Supplementary European Search Report for the Application No. EP 03 80 8895 dated Oct. 9, 2009.

* cited by examiner

LIQUID PORTIONING METHOD AND DEVICE

This application is a 371 of PCT/JP03/12447, filed on Sep. 29, 2003.

BACKGROUND OF THE INVENTION

2. Field of the Invention

The present invention relates to methods and apparatuses for dispensing samples or reagents in analysis apparatuses for use in the fields of chemistry, industry, clinical technology, and biotechnology.

2. Description of the Related Art

Laser desorption/ionization mass spectrometry methods have been performed which apply laser light to samples placed on sample plates mounted in a mass spectrometry apparatus to ionize and analyze the samples. Some of the spectrometry methods employ matrix in creating samples on sample plates, while other spectrometry methods employ no matrix.

The methods which combine such spectrometry methods employing matrix and a time of flight mass spectrometry apparatus are called MALDI-TOF (matrix-assisted laser desorption/ionization mass spectrometry-time of flight) mass spectrometry methods. In MALDI-TOFs, a test sample is dripped onto sample plates along with a matrix solution and detection is conducted after drying them.

On the other hand, there has been suggested a mass spectrometry method which utilizes a small-quantity dispensing technique using piezo devices for causing various reactions on membranes and uses the reaction products, wherein as target samples, biomolecules are separated by electrophoresis, transferred to the membranes and solidified in the membranes (see, international publication No. WO98/47006).

As a method for detecting materials spread and solidified on a membrane, there is immunobloting method. The immunobloting method, generally called western bloting method, is a method which spreads protein samples or the like by electrophoresis, solidifying them in a membrane and causing reaction with specific antibodies as probes for the target materials, thus detecting the presence thereof.

A reagent or sample is dispensed onto a target object, such as a sample plate or a membrane secured on a sample plate, with a dispensing mechanism having a piezo device or the like (referred to as a dispensing device). Then, the sample plate, etc., is transferred to another apparatus, such as a mass spectrometry system or other analysis apparatuses or preparation apparatuses, for performing analyses or subsequent processes.

It is necessary at first that a reagent or sample is accurately dispensed only onto the spot spread on a sample plate or a membrane.

It is preferred that the dispensing device is capable of being replaced in the event of clogging of the dispensing device of the dispensing mechanism or in order to enable dispensing other samples or reagents. In such a case, the dispensing device may be displaced from a predetermined position when the dispensing device is newly mounted or replaced.

When a sample plate, onto which a reagent or sample has been dispensed, is transferred to a subsequent analysis apparatus or processing apparatus, it is necessary to know precisely the position to which the reagent, etc., has been dispensed.

It is commonly required to know the position information after processes are applied to a target object, in various analysis apparatuses and processing apparatuses, not only in liquid dispensing apparatuses.

In the field of analysis apparatuses which mainly utilize liquid-phase materials, regardless of samples or reagents, attempts have been made to reduce the amount of solutions used in analyses. This is because reduction of solutions is effective in reducing the waste of important samples and in reducing the amounts of expensive reagents used, and also it is an effective approach for improving the process efficiency of experiments, since the smaller the amounts of solutions used for biochemical reactions, the shorter the time required for completing the reactions.

In order to cause reactions using small amounts of solutions, there is a need for a dispensing apparatus for dispensing small amounts of samples or reagents. Various methods have been put into prace, as methods for dispensing small amounts of liquids, such as methods using a piezoelectric device such as a piezo device, methods using the opening and closing of valves, and methods utilizing air bubbles which are created by locally heating solutions.

In order to dispense small amounts of liquid onto target positions, there is a need for delicate control of various parameters such as the way of voltage application to a piezoelectric device or the opening time and closing time of a valve. In order to optimize the parameters and further to monitor the shapes of dispensed liquid drops for coping with environmental changes or changes in the piezoelectric device with time since it takes a long time to dispense liquid onto plural positions, images of liquid drops formed at the tip end of the dispensing device are captured and monitored by an image capturing device.

FIG. 16 illustrates a conventional dispensing apparatus with an image capturing device for monitoring the tip end of the dispensing head.

Reference numeral 102 denotes a dispensing mechanism for dispensing a reagent and the dispensing mechanism includes a nozzle at its lower end for dripping a small amount of reagent An X-Y table 104 is placed under the dispensing mechanism 102 and a target object, onto which a reagent is to be dispensed, is placed on the X-Y table 104. The X-Y table 104 can be moved in an X direction and a Y direction within a horizontal plane to position the reagent dispensing position on the target object beneath the nozzle of the dispensing mechanism 102.

Reference numeral 106 denotes an image capturing device for monitoring the conditions of liquid drops formed at the nozzle tip end, and a light source 108 is placed opposite to the image capturing device 106 for enabling monitoring using transmitted images.

In order to accurately dispense liquid onto a target dispensing position, it is preferable that the distance between the dispensing nozzle tip end and the target object is small. Therefore, the image capturing device 106 for monitoring the condition of dispensing is horizontally installed, that is to say, installed at the same height as the nozzle tip end.

Furthermore, in order to dispense liquid stably onto a plurality of positions on the target object, the target object is put on a movable table such as an X-Y table 104, as illustrated in FIG. 16.

In order to install the image capturing device 106 horizontally, and, also in order to prevent interference between the X-Y table 104 and the image capturing device 106, it is necessary that the image capturing device 106 is mounted outside the range of movement of the X-Y table 104, which upsizes the apparatus.

As a dispensing apparatus including a piezo chip, there is a dispensing unit including a piezo chip having a downward opening at its discharging portion. Such a piezo chip is configured to discharge liquid drops from its discharging portion when a driving section including a piezo device pushes the liquid charged in a space communicated to the discharging portion.

When small amounts of liquid are dispensed from the piezo chip in such a dispensing apparatus, it is necessary to maintain the condition where liquid is charged to the tip end of the piezo chip and there is no excess liquid at the tip end thereof. Otherwise desired amounts of liquid can not discharged.

Therefore, conventionally, the piezo chip tip end is photographed by a CCD camera, etc., during test dispensation prior to the start of dispensation. Then, the captured image is displayed in an enlarged manner, and liquid is manually charged by referring to the image and, when excess liquid is leaked from the tip end, the liquid is wiped away.

However, with such conventional methods utilizing manual operations, experience was required to successfully achieve the charging of liquid into the piezo chip and there has been difficulty in creating liquid drops with intended sizes.

Dispensation of small amounts of sample liquid or reagent liquid on the order of picoliters to microliters have been performed by piezo systems or syringe systems.

A dispensing apparatus utilizing a piezo system includes a piezo chip 302 having a discharging portion at its tip end, as illustrated in FIG. 17. In the piezo chip 2, a driving section including a piezo device pushes a liquid reservoir communicated to the discharging portion to discharge liquid drops 306 from the discharging portion. In order to control the driving section for discharging liquid drops of a constant size, a piezo dispensing control section 304 is provided. Liquid drops 306 are discharged from the piezo chip 302 according to parameters for driving the piezo device, which are set in the piezo dispensing control section 304.

In a dispensing apparatus utilizing a syringe system, as illustrated in FIG. 18, liquid drops 6 are discharged from a probe 312 connected to a syringe pump 310 by driving a motor 314 for operating the syringe pump 310. A disposable chip 316 at the tip end of the probe 312 may be provided. The chip 316 is replaced for each sample or reagent A syringe dispensing control section 318 controls the driving of the motor 314 so that operation parameters for the syringe pump 310 become equal to set values to discharge liquid drops 306 with a predetermined size.

The condition of discharging is set depending on the properties, such as the viscosity, of the sample or reagent to be discharged. However, the size of discharged liquid drops varies with environmental changes such as the temperature. Furthermore, the smaller the amount of liquid drops, the poorer the quantifying accuracy.

It is an object of the present invention to enable accurately dispensing liquid onto positions to which liquid is to be dispensed.

SUMMARY OF THE INVENTION

It is a first aspect of the present invention to achieve the aforementioned object by a dispensing apparatus capable of designating the dispending position and capable of automatically dispensing liquid onto the designated position.

A dispending apparatus according to the first aspect comprises: a dispensing mechanism including a dispensing device for dripping a sample or a reagent; an image capturing device for capturing the downward area image; a movable table capable of supporting, on its upper surface, a target object onto which the sample or reagent is to be dispensed and being moved on a horizontal plane surface for positioning the target object at least at a dispensing position beneath the dispensing device and at an image capturing position beneath the image capturing device; a monitoring section for displaying the image captured by the image capturing device; a dispensing position designating section for designating the dispensing position on the target object based on the image of the target object displayed on the monitoring section; and a dispensing control section for positioning the target object and the dispensing device relative to each other so that the dispensing position on the target object designated by the dispensing position designating section is placed beneath the dispensing device of the dispensing mechanism and for controlling the dispensing operation of the dispensing mechanism.

With the dispensing apparatus according to the first aspect, the image captured by the image capturing device is displayed on the monitoring section and, based on the image of the target object displayed on the monitoring section, the dispensing position on the target object is designated. Thus, the dispensing control section positions the target object and the dispensing device relative to each other and controls the dispensing operation of the dispensing mechanism. Consequently, by designating the dispensing position on the image displayed on the monitoring section, a reagent or a sample is automatically dispensed onto the designated position.

The dispensing mechanism may include a plurality of dispensing devices for enabling dispensing a plurality of reagents or samples onto a single dispensing position or different dispensing positions.

The dispensing apparatus may further include a dispensing position information creating section for creating dispensing position information about the dispensing positions, which are designated by the dispensing position designating section and to which the dispensing operation has been performed, on the target object This enables preserving information of the positions on the target object to which the reagent or sample has been dispensed.

Also, the dispensing position information creating section may be configured to be capable of outputting the created dispensing position information to the outside. The target object onto which reagent or sample has been dispensed is transferred to an analysis device such as a mass spectrometry device or transferred to a preparation device as required. In such a case, the analysis device or the preparation device to which the target object is transferred can capture the dispensing position information created and output by the dispensing position information creating section to know the positions on the target object onto which reagent or sample has been dispensed. Consequently, the analysis device or the preparation device can easily perform operations such as performing analyses on the dispensing positions or applying preparation to the dispensing positions.

The dispensing position designating section may be configured to designate the dispensing positions on the image of the target object displayed on the monitoring section, for example, with a cursor.

The dispensing apparatus may further include an image capturing device for photographing the tip end of the dispensing device, in order to monitor the dispensing operation and adjust the amount of liquid discharged from the dispensing device. In this case, when the dispensing mechanism includes a plurality of dispensing devices, the image capturing device is supported on a moving mechanism so that it is capable of being moved in association with the switching of the dispensing device performing the dispensing operation to photograph the tip end of the dispensing device which is performing the dispensing operation.

It is a second aspect of the present invention to achieve the aforementioned object by enabling accurate dispending operations even when the dispensing device has been newly mounted or replaced.

A dispensing apparatus according to the second aspect comprises: a dispensing mechanism including a detachable dispensing device for dripping a sample or reagent; an image capturing device for capturing a downward area image; a movable table capable of supporting, on its upper surface, a target object onto which the sample or reagent is to be dispensed and being moved on a horizontal plane surface for positioning the target object at least at a dispensing position beneath the dispensing device and at an image capturing position beneath the image capturing device; and a calibrating section which, after liquid is dispensed onto a predetermined position on the movable table by the dispensing mechanism, detects the dispensing position based on the image captured by the image capturing device and calibrates the dispensing position based on base points serving as references on the movable table, the base points being captured concurrently with the image.

The dispensing device of the dispensing mechanism is mounted on a predetermined position. However, in order to cause the dispensing device to be mounted at the same position any time, there is a need for excellent machining accuracy of the dispensing device mounting portion. Furthermore, individual dispensing devices are mechanically different from one another. Therefore, in order to adjust the mounting of the dispensing device so that the dispensing position is brought into coincidence with a predetermined position, there is a need for excellent machining accuracy and excellent adjusting technique.

However, with the liquid dispensing apparatus according to the second aspect, the dispensing mechanism includes the detachable dispensing device, and, after liquid is dispensed onto a predetermined position on the movable table by the dispensing device, the dispensing position is detected based on the image captured by the image capturing device and calibrated based on base points serving as references on the movable table, the base points being captured concurrently with the image. This simplifies adjustment operations involved in the mounting or replacement of the dispensing device.

The second aspect also includes a dispensing apparatus including a plurality of dispensing devices and, in this case, the calibrating section performs the calibration on the respective dispensing devices.

It is a third aspect of the present invention to achieve the aforementioned object by a position information capturing device for creating accurate information about the positions to which liquid has been dispensed or other processes have been applied.

The position information capturing device according to the third aspect includes an image capturing device for capturing an image of a target object on a table; and a position information creating section for creating, based on the image captured by the image capturing device, information about positions designated or detected in the image, based on a plurality of reference points serving as references on the target object Also, when information about the designated positions on the target object is provided, the position information capturing device may further include a monitoring section for displaying the image captured by the image capturing device; and a position designating section for designating positions on the target object based on the image of the target object displayed on the monitoring section; wherein the position information creating section creates information about the positions on the target object designated by the position designating section.

Since the position information capturing device creates, based on the image captured by the image capturing device, the information about positions designated or detected in the image, based on a plurality of reference points serving as references on the target object, the position information on the target object can be accurately determined based on the reference points.

Further, even when the target object is transferred to an analysis apparatus, etc., it is possible to accurately position the analysis apparatus with respect to the target position on the target object from the position information based on the reference points.

The image capturing device may be configured to capture an image of the table along with the image of the target object and the position information creating section may create position information on the target object based on a plurality of base points serving as references on the table. This enables accurately determining information about the target position on the target object based on the base points. Furthermore, even if the target object is removed from the table and then mounted on the table again, the dispensing device can be accurately positioned with respect to the target position on the target object from the position information based on the reference points.

Also, the position information creating section may be configured to be capable of outputting the created position information to the outside and, in such a case, even when the target object is transferred to another apparatus such as an analysis apparatus, it is possible to accurately position other apparatuses with respect to the target position from the position information.

It is a fourth aspect of the present invention to achieve the aforementioned object by a sample plate which enables creating accurate information about the position to which liquid has been dispensed or other processes have been applied.

The sample plate according to the forth aspect, which is advantageous in providing accurate position information, is a plate-shaped member having a surface onto which a sample or reagent is to be dispensed and the surface includes, thereon, a plurality of marks serving as positional references.

Since the sample plate includes a plurality of marks serving as positional references on the surface onto which sample or reagent is to be dispensed, it is advantageous in creating accurate position information about the dispending position on the sample plate.

It is a fifth aspect of the present invention to miniaturize the dispensing apparatus and also attain the aforementioned object by providing a mechanism for monitoring the condition of dispensation.

The dispensing apparatus according to the fifth aspect comprises: a dispensing mechanism including a nozzle for dripping a sample or a reagent; a movable table capable of supporting, on its upper surface, a target object onto which the sample or reagent is to be dispensed and being moved on a horizontal plane surface for positioning the target object beneath the nozzle; and an image capturing device placed, in a plane, within the range of movement of the movable table and mounted at a position above the movable table for preventing contact therewith, wherein the image capturing device photographs the tip end of the nozzle at an angle from above.

Since the image capturing device for monitoring the condition of dispensation is placed obliquely above the movable table at an angle with respect to the horizontal direction, the image capturing device can be installed within the range of movement of the movable table without causing interference with the movable table, which may miniaturize the dispensing apparatus.

A light source may be placed at the position opposite to the image capturing device with respect to the tip end of the nozzle and, in this case, the light source is oriented in such a direction that light emitted from it is reflected at the surface of the target object, then passes through the tip end of the nozzle and then enters the image capturing device. Provision of such a light source enables monitoring a drop of a sample or a reagent formed at the nozzle tip end by capturing an image of the drop using the transmitted light, thus providing a clear image and enabling accurate monitoring.

The image capturing device may be set to capture an image of the surface of the target object beneath the nozzle along with the image of the tip end of the nozzle. In such a case, it is possible to monitor the condition of the target object surface as well as the nozzle tip end, thus providing more information. For example, it is possible to confirm whether or not the sample or reagent could be dispensed appropriately onto the target position. Also, in the case where a sample or reagent is dispensed onto a film which is a target object, it is possible to observe the conditions of the film before and after dispensation or observe the time-varying film condition during the reaction.

It is a sixth aspect of the present invention to attain the aforementioned object by facilitating the adjustment of the amount of liquid at the piezo chip tip end before the start of dispensation, in a dispensing method and a dispensing apparatus using a piezo chip.

The dispensing method according to the sixth aspect utilizes a dispensing unit and the dispensing unit includes a piezo chip having a downward opening portion at its discharging portion and being configured to discharge liquid drops from the discharging portion when liquid charged in a space communicated to the discharging portion is pushed by a driving section including a piezo device, a pressure control mechanism for adjusting the pressure of the liquid charged in the space, and an image capturing device for capturing an image of the discharging portion. The method includes the steps of capturing and storing the image of the discharging portion before charging liquid in the space by the image capturing device; after charging liquid in the space, capturing the image of the discharging portion by the image capturing device, determining the difference between the images and controlling the pressure control mechanism so that, when liquid exits from the discharging portion, the liquid is retracted until the difference between the images is cancelled, in a preparation stage before the start of dispensation operation from the piezo chip.

The image of the piezo chip tip end captured before charging liquid in the piezo chip represents a state where liquid does not appear from the discharging portion, which is a state serving as a reference in charging liquid into the piezo chip. Then, liquid is charged in the piezo chip and a pressure is applied to the liquid through the pressure control mechanism to supply the liquid to the discharging portion of the piezo chip, thus causing a state where liquid has been charged. The images of the discharging portion of the piezo chip are captured from the start of liquid charging and differences between the images and the image captured before the charging of liquid. The liquid is gradually pressurized by the pressure control mechanism and when it is confirmed from the differences in the images that excess liquid appears from the discharging portion, the pressure control is changed to feedback control to cause negative pressure from the pressure control mechanism. Then, when there appears no excess liquid, the pressure control is fixed. Thus, the preparation before the dispensation operation is completed and dispensation is started in this state.

When these processes are automatically performed using a control device, the pressure adjustment can be automatically achieved to reach a condition which enables dispensation using a piezo chip, and it is only required to start the charging of liquid in the piezo chip.

The dispensing apparatus according to the present invention for performing the dispensing method of the sixth aspect comprises: a dispensing unit including a piezo chip having a downward opening portion at its discharging portion, the piezo chip being configured to discharge liquid from the discharging portion when liquid charged in a space communicated to the discharging portion is pushed by a driving section including a piezo device, a pressure control mechanism for adjusting the pressure of the liquid charged in the space; an image capturing device for capturing an image of the discharging portion; a storing device for storing images captured by the image capturing device; and a control device which compares the image of the discharging portion captured before charging liquid in the space and stored in the storing device with images captured after charging liquid in the space and controls the pressure control mechanism so that, when liquid exits from the discharging portion, the liquid is retracted until the differences between the images and the image captured before charging liquid is cancelled.

The image capturing device may be installed so that it captures the image of the discharging portion along a horizontal direction, which enables more accurately charging liquid in the piezo chip.

Conventionally, there has been a need for delicate manual pressure control by referring to the image of the piezo chip Up end. However, with the present invention, the image of the discharging portion is captured by the image capturing device and stored prior to charging liquid in the piezo chip, and, after the start of charging of liquid, images of the discharging portion are captured by the image capturing device and the differences between the images and the image captured before the charging of liquid are determined. The pressure control mechanism is controlled so that, when the liquid appears from the discharging portion, the liquid is retracted until the difference between the images and the image captured before the charging of liquid is cancelled. This enables easily achieving the adjustment of the amount of liquid at the piezo chip tip end.

When these processes are automatically performed using the control device, the pressure adjustment can be automatically achieved to reach a condition which enables dispensation using a piezo chip, and it is only required to start the charging of liquid in the piezo chip. Furthermore, when such monitoring is continuously performed at standby state, the condition of the piezo chip tip end can be maintained constant.

It is a seventh aspect of the present invention to achieve the aforementioned object by improving the quantifying accuracy of dispensation of small amounts of sample liquid and reagent liquid.

The quantifying dispensing method according to the seventh aspect acquires an image of a liquid drop discharged from the discharging portion of the dispensing unit, determines the size of the liquid drop from the image and controls the amount of dispensed liquid drop.

That is to say, the quantifying dispensing method includes the following steps (A) to (C).

(A) acquiring the image of the liquid drop discharged from the discharging portion;

(B) determining the size of the liquid drop based on the captured image; and (C) adjusting parameters of control signals output to a discharging driving section of the dispensing unit, based on the determined size of the liquid drop, so that the amount of the liquid drop to be dispensed becomes equal to a predetermined value.

This improves the quantifying accuracy in dispensation of small amounts of sample liquids or reagent liquids on the order of picoliters to microliters.

The size of the liquid drop determined in the step (B) is, for example, the diameter or the radius of the liquid drop.

The step for determining the size of the liquid drop may be performed by automated calculation using image processing. Such image processing programs can be easily obtained. The use of automated calculation with image processing enables rapid and accurate determination of the size of the liquid drop.

The step for determining the size of the liquid drop may be performed by manual calculation on the image. The use of manual calculation can save the cost for image processing programs.

The dispensing unit may utilize a piezo-dispensing system including a piezo head and the piezo head may be configured to discharge liquid drops from the discharging portion when liquid charged in a space communicated to the discharging portion at its tip end is pushed by a driving section including a piezo device. In this case, the parameters of control signals include at least one of the amplitude of the voltage applied to the piezo device, the rising time of the applied voltage, the voltage application time period, and the descending time of the applied voltage.

The dispensing unit may utilize a syringe-pump dispensing system and, in this case, the parameters of control signals may include at least one of the stroke, the speed and the acceleration of the plunger of the syringe pump.

In the case of a syringe-pump dispensing system, the image for determining the size of the liquid drop may be an image of a ball-shaped liquid drop at the tip end of the discharging portion.

The step of adjusting parameters of control signals may be performed by automated control using a control section for controlling the discharging driving section, which may reduce the number of processes performed by operators.

The step of adjusting parameters of control signals may be performed by inputting to the control section for controlling the discharging driving section, which may simplify the system.

DESCRIPTION OF THE PREFERRED EMBODIMENTS

Figure 1:
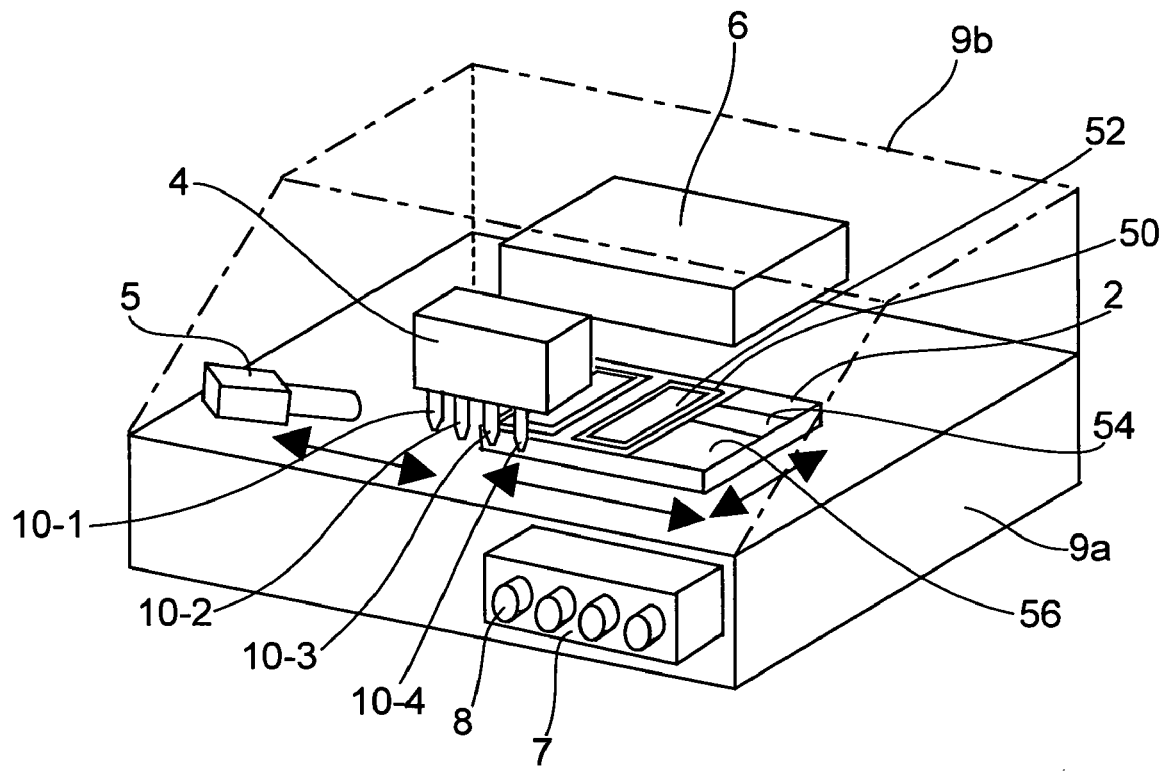
FIG. 1 is a perspective view schematically illustrating an embodiment of a dispensing apparatus.

FIG. 1 schematically illustrates an embodiment of a liquid dispensing apparatus according to the present invention.

Reference numeral 4 denotes a print head which is a dispensing mechanism and includes four dispensing devices 10-1 to 10-4 arranged in a row and mounted thereto, each dispensing device including a piezo device for dispensing a reagent, etc. The dispensing devices 10-1 to 104 are in fixed positions. In order to control the amounts of liquid dispended from the dispensing devices 10-1 to 10-4, a pressure control section 7 for adjusting the pressure applied on the dispensing devices is mounted to the front surface of the apparatus main body, and four knobs 8 for adjusting the pressures within the dispensing devices 10-1 to 10-4 are arranged in correspondence with the respective dispensing devices 101 to 10-4.

A scanner 6, as an image capturing device, is placed for capturing images of a table and sample plates onto which liquid is to be dispensed. The scanner 6 is also fixedly positioned.

The table 2 is a movable table capable of being moved within a horizontal plane. As will be illustrated later in FIG. 2, sample plates 50 are put on the table 2 at predetermined positions. The table 2 is moved within a plane to position a designated point of the sample plates 50 beneath the dispensing devices 10-1 to 10-4 during dispensation and to position a portion of the table 2 to be photographed beneath the scanner 6 during capturing images.

A CCD camera 5, as an image capturing device, is placed for capturing images of the tip ends of the dispensing devices 10-1 to 10-4 and monitoring the conditions of dispensation from them during dispensation from the dispensing devices 10-1 to 10-4. In order to save the installation space of the CCD camera 5, the CCD camera 5 is mounted so that it captures images of the tip ends of the dispensing devices 10-1 to 10-4 at an angel from above. The dispensing devices 10-1 to 10-4 dispense different liquids and any of the dispensing devices 10-1 to 10-4 beneath which a predetermined dispensing position of the sample plates 50 is positioned performs the dispensing operation. The camera 5 is mounted to be capable of being moved in parallel with the arrangement of the dispensing devices 10-1 to 10-4 so that, when the dispensing device 10-1 to 10-4 which performs the dispensing operation has been switched, it can capture an image of the dispensing device 10-1 to 10-4 performing the operation.

The table 2, the print head 4, the camera 5 and the scanner 6 are housed within a casing constituted by a main body 9*a* and a cover 9*b*, and the cover 9*b* of the casing can be opened any time, for example, when replacing the sample plates 50.

Figure 2:
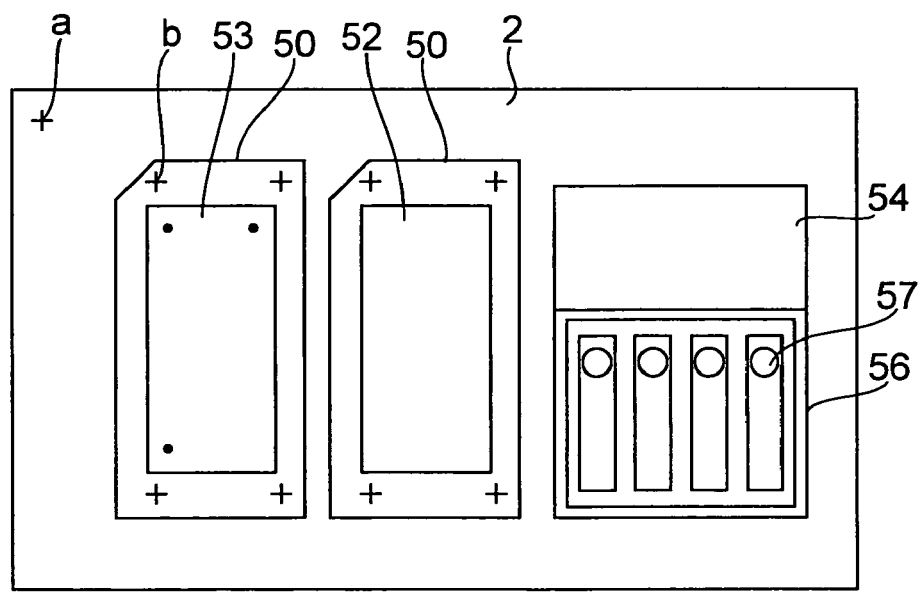
FIG. 2 is a plan view illustrating the upper surface of a table on which sample plates and other components are placed in the present embodiment

FIG. 2 illustrates sample plates and other components placed on the table 2.

Two sample plates 50 can be put on it so that they are secured at predetermined positions. Reference numeral 52 is a membrane attached onto the sample plate 50, and a reagent or sample is dispensed onto the membrane 52 in the dispensing apparatus. The sample solidified in the membrane 52 may be molecules of protein, peptide, sugar, lipid, nucleic acid or combinations thereof, which have been separated and spread in a one-dimensional direction by, for example, SDS (sodium dodecyl sulfate) polyacrylamide gel electrophoresis or other chromatography.

The solidification of the sample into the membrane 52 can be achieved by spreading the sample in a gel or other migration mediums and then transferring it to the membrane 52.

The material of the membrane used for such solidification may be PVDF (polyvinylidene difluoride), nitrocellulose, nylon (registered trademar), derivatives thereof, etc.

In order to detect the materials within the spots spread and solidified on the membrane 52, the dispensing devices 10-1 to 10-4 may dispense digestive reagents or extracting reagents onto the solidified samples in the membrane 52.

It may also dispense a material serving as a probe which combines with to-be-detected molecules. An antibody is used as such a probe, in the case where the to-be-detected molecules are antigens. In general, biomaterials which idiosyncratically react with the to-be-detected molecules may be employed. Also, combinations of some antibodies and some biomaterials may be employed.

Preferably, reagents are dispensed only onto the spots on the membrane 52, which can reduce wastes of the reagents.

In order to enable optical detection of to-be-detected material, it may employ a primary reagent containing a probe which idiosyncratically reacts with the to-be-detected material and a secondary reagent which colors the to-be-detected material after the reaction with the probe, as the reagent to be dispensed. In this case, the primary reagent is first dispensed from any one of the dispensing devices 10-1 to 10-4 and then the secondary reagent is dispensed from another one of the dispensing devices 10-1 to 10-4 onto the region to which the primary reagent has been dispensed. Such a secondary reagent may be a coloring reagent or a fluorescent reagent Furthermore, as an appropriate method for detecting the to-be-detected molecules after the reaction with the probe, it is possible to cause reaction of the to-be-detected molecules with metal ions, as well as dispensing a coloring reagent or a fluorescent reagent, and it is also possible to combine these methods. As such methods, there is a method utilizing a colloidal gold labeling antibody and a method which causes a reaction with a fluorescent reagent and a protein, etc., having an affinity for metal ions utilizing $Ni^{2+}$ chelate enzyme.

Since plural dispensing devices 10-1 to 10-4 are provided, it is possible to dispense plural reagents by switching between the dispensing devices 10-1 to 10-4 by moving the dispensing position on the sample plates 50 through the table 2.

A plurality of marks "b" are provided on the respective sample plates 50. These marks "b" are reference points serving as references for creating information of the dispensing point on the membrane 52 attached to the sample plates 50. In this case, the reference points "b" are provided at the four corners of a substantially rectangular shape, and the scanner 6 captures these reference points "b" along with images of the membrane 52. One of the corners of each sample plate 50 is cut out for designating the orientation of the sample plate 50.

A region 54 on the table 2 is provided as a test printing region for conducting dispensation tests of the dispensing devices 10-1 to 10-4. Filter papers are attached to the region 54 for verifying the dispensing condition by the CCD camera 5 during test printing.

The region 56 provided on the table 2 is a maintenance region for the dispensing devices 10-1 to 10-4 and sponges 57 are provided therein. In the event that liquid or contaminations have been adhered to the tip ends of the dispensing devices 10-1 to 10-4, the maintenance region is moved beneath the dispensing devices 10-1 to 10-4 and the liquid or contaminations adhered to the tip ends of the dispensing devices 10-1 to 10-4 are wiped away by the sponges 57.

Furthermore, a mark "a" is provided on the surface of the table 2 as a base point which serves as a reference for the positions of the sample plates 50 placed on the table 2. The mark "a" serves as a reference when extracting information of the dispensing position, and also serves as a reference for enabling matching between positions on images captured by the scanner 6 and the movement of the table 2. The dispensing devices 10-1 to 10-4 in the head 4 have the same configuration.

As an exemplary liquid dispensing apparatus used for small-quantity dispensing systems, there is a dispensing apparatus utilizing a dispensing system using piezo devices as described above. Such a liquid dispensing apparatus is configured so that a reagent is charged in a space communicated to the discharging portion at the tip end thereof, and liquid drops of the reagent are discharged from the discharging portion by pushing the reagent through a driving section including a piezo device. In such a case, the parameters of control signals may include at least one of the amplitude of the voltage applied to the piezo device, the rising time of the applied voltage, the voltage application time period, and the descending time of the applied voltage.

Also, as a liquid dispensing apparatus similar to this, it may also utilize a liquid dispensing apparatus employing liquid discharging devices as those used in ink-jet type liquid discharging apparatuses.

As another exemplary liquid dispensing apparatus used in small-quantity dispensing systems, it also may employ an apparatus utilizing a syringe-pump dispensing system. In this case, the parameters of control signals may include at least one of the stroke, the speed and the acceleration of the plunger of the syringe pump.

Figure 3:
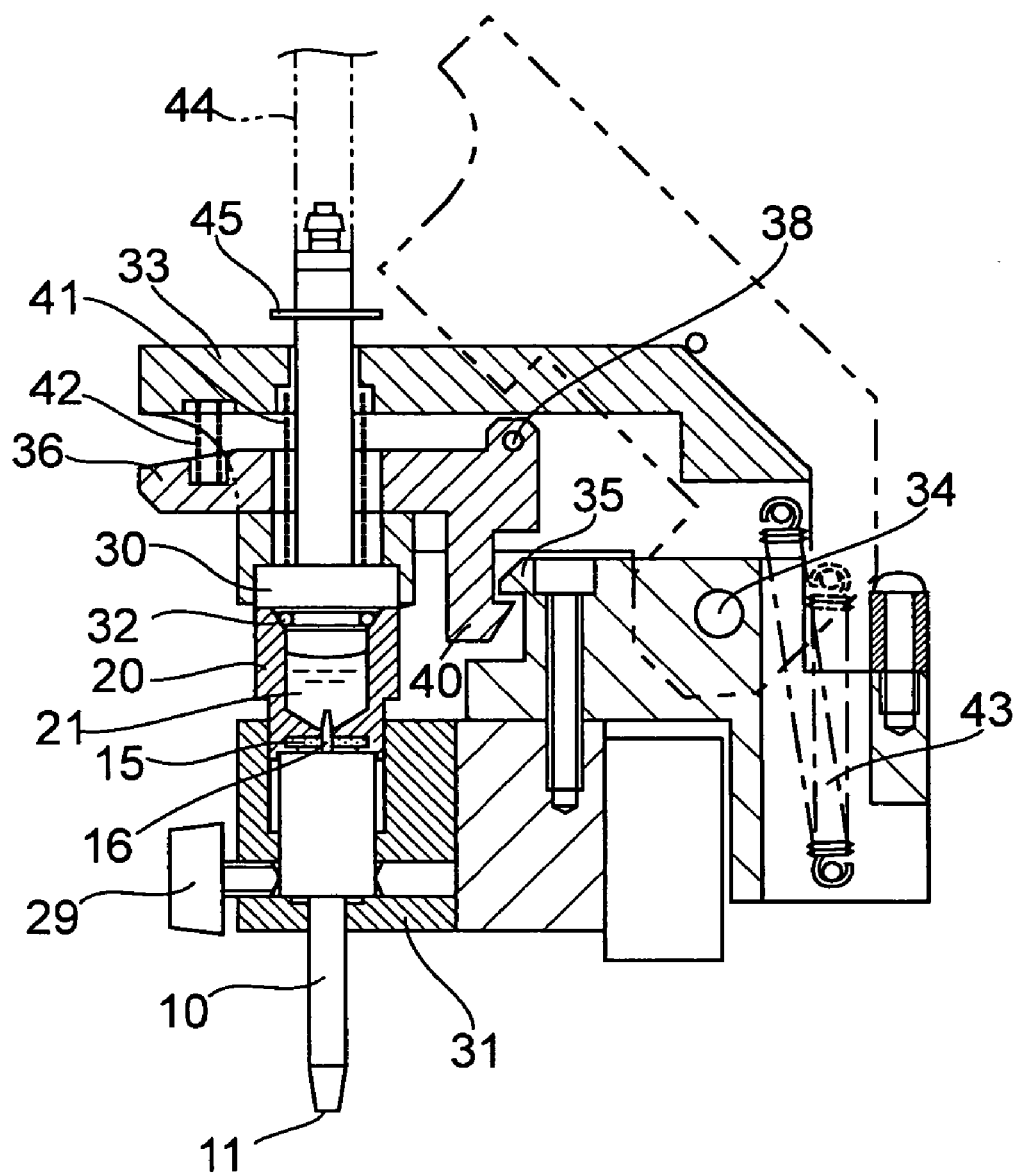
FIG. 3 is a cross sectional view illustrating a dispensing mechanism according to the present embodiment.

With reference to FIG. 3, an exemplary dispensing mechanism including a piezo chip 10 which contains a piezo device as a dispensing device will be described in detail.

A piezo chip 10, as a liquid discharging portion, which has a discharging port at its lower end and a hollow needle 16 at its upper end is detachably mounted to a chip retaining portion 31 of the liquid dispensing apparatus by a bolt 29. The piezo chip 10 can be detached from it by loosening the bolt 29 and it can be secured thereto by fastening the bolt 29. When the piezo chip 10 is attached or detached, the dispensing position is displaced. Therefore, as will be described later, the dispensing position is calibrated with reference to the base point "a" on the table 2, in the present embodiment.

A dispensation liquid container 20, which is a disposable container, includes openings at its lower and upper ends and contains therein dispensation liquid by closing the lower-end opening with a cover 15. The cover 15 at the lower-end opening is an elastic septum made of an elastic material which allows the hollow needle 16 of the piezo chip 10 to penetrate it and, after the hollow needle 16 has been pulled out after penetration, can close the through hole with its elasticity. The elastic material constituting the cover 15 is, for example, rubber.

When the container 20 is mounted on the chip 10 and the hollow needle 16 has been penetrated through the cover 15 at the lower-end opening thereof, an air-introducing head 30 can be mounted from above the container 20. The air-introducing head 30 is configured to adjust the pressure within the container 20 for adjusting the amount of liquid discharged from the chip 10.

The air-introducing head 30 includes a sealing member 32 at its end. The sealing member 32 is, for example, an O-ring. By pushing down the air-introducing head 30 against the container 20, the sealing member 32 can be brought into contact with the inner surface of the opening of the container 20 to hermetically seal the opening of the container 20, which enables controlling the pressure within the container 20 through air supplied from a pressure control mechanism to the air-introducing head 30.

An arm mechanism for detachably mounting the air-introducing head 30 is provided. The arm mechanism includes an arm 33 and a lock 36 and the air-introducing head 30 is retained by one end of the arm 33. The arm 33 is rotatably supported, at its base end, on the liquid dispensing apparatus main body through a pin 34. The lock 36 is rotatably supported on the arm 33 through a pin 38 and provided with a hook 40 at its base end. The hook 40 is configured to be capable of engaging with a protrusion 35 secured to the liquid dispensing apparatus main body to be locked with the container 20 mounted on the chip 10.

The air-introducing head 30 is slidably inserted through a hole perforated through the arm 33 and then the air-introducing head 30 is biased and pushed towards the container 20 by a spring 41. The base end of the air-introducing head 30 is protruded from the arm 33 and is provided with a coller 45 for preventing the air-introducing head 30 from being pulled out of the arm 33. The base end of the air-introducing head 30 is connected to the pressure control mechanism through a pipe 44.

In order to bias the lock 36 about the pin 38 in such a direction that the hook 40 engages with the protrusion 35, a coil spring 42 being compressed is inserted between the arm 33 and the lock 36.

A spring 43 is hooked between the arm 33 and the liquid dispensing apparatus main body so that the spring 43 biases the arm 33 in such a direction that it opens (in the clockwise direction in the figure).

In the mechanism of FIG. 3, when the container 20 is mounted thereto, the container 20 is placed on the chip 10 and pushed down to cause the hollow needle 16 to be penetrated through the septum 15 and to be immersed in the liquid within the container 20. By rotating the arm 33 in the counterclockwise direction in the figure, the air-introducing head 30 is mounted to the opening of the container 20 and is hermetically coupled to the container 20 through the sealing member 32, since the air-introducing head 30 is retained by the arm 33. At this time, the hook 40 engages with the protrusion 35 to lock the arm 33, thus preventing the arm 33 from rotating in the clockwise direction to be opened. Since the spring 41 biases and pushes the air-introducing head 30 towards the container 20, the hermetic coupling between the container 20 and the head 30 can be maintained while the arm 33 is locked.

In this state, liquid can be discharged from the chip 10.

When the container 20 is detached from it, the lock 36 is pushed towards the arm 33. The lock 36 is rotated in the clockwise direction in the figure about the pin 38, thus releasing the engagement between the hook 40 and the protrusion 35. Thus, the arm 33 is rotated in the clockwise direction in the figure by the force of the spring 43, thereby causing the air-introducing head 30 to separate from the container 20.

At this time, the air-introducing head 30 is rotated together with the arm mechanism about the pin 34 to produce a large gap between the air-introducing head 30 and the container 20, which facilitates maintenance such as cleaning of the sealing member 32 of the air-introducing head 30 or the periphery of the container 20.

Furthermore, since the air-introducing head 30 is configured to be attachable to and detachable from the container 20 through the arm mechanism as described above, it is possible to easily achieve the attachment and detachment of the container 20 and the attachment and detachment of the air-conducting head 30 to and from the container 20.

Returning to FIG. 1, the CCD camera 5 will be described.

In the fields of analysis devices which mainly utilize liquid-phase materials, regardless of samples or reagents, there have been made attempts to reduce the amounts of solutions used in analyses. This is because reduction of solutions is effective in reducing the waste of important samples and in reducing the amounts of used expensive reagents, and also it is an effective approach for improving the process efficiency of experiments, since the smaller the amounts of solutions used for biochemical reactions, the shorter the time required for completing the reactions.

In order to cause reactions using small amounts of solutions, there is a need for a dispensing apparatus for dispensing small amounts of samples or reagents. Various methods have been put into practice, as methods for dispensing small amounts of liquids, such as methods using a piezoelectric device such as a piezo device as in the present embodiment, methods using the closing and opening of valves and methods utilizing air bubbles which are created by locally heating solutions.

In order to dispense small amounts of liquid onto target positions, there is a need for delicate control of various parameters such as the way of voltage application to a piezoelectric device or the opening time and closing time of a valve. In order to optimize the parameters and also in order to monitor the shapes of dispensed liquid drops for coping with changes in an environment where the dispensing device is installed or changes in the piezoelectric device with time since it takes a long time to dispense liquid onto plural positions, it is preferable that images of liquid drops formed at the tip end of the dispensing device are captured and monitored by an image capturing device. The CCD camera 5 is an example of such an image capturing device.

Since the CCD camera 5 for monitoring the condition of dispensation is placed obliquely above the dispensing devices at an angle with respect to the horizontal direction, the CCD camera 5 can be installed within the range of the movement of the movable table 2 without causing interference thereof with the movable table 2, which enables miniaturization of the dispensing apparatus.

Also, a light source may be placed at the position opposite the CCD camera 5 with respect to the tip ends of the dispensing devices and, in this case, the light source is oriented in such a direction that light emitted from it is reflected at the surface of the sample plate 50 which is the target object, then passes through the tip end of the dispensing device and then enters the CCD camera 5. Provision of such a light source enables monitoring drops of a sample or a reagent formed at the tip end of the dispensing device by capturing images of drops using the transmitted light, thus providing clear images and enabling accurate monitoring. Furthermore, the light source may be turned on in synchronization with the timing of dispensation to capture images of liquid drops as though they were static images.

Also, the CCD camera 5 may be set to capture images of the sample plate surface beneath the dispensing device along with images of the dispensing device tip end. In such a case, it is possible to monitor the condition of the sample plate surface as well as the dispensing device tip end, thus providing more information. For example, it is possible to confirm whether or not the sample or reagent could be dispensed onto the target position. Also, in the case where a sample or reagent is dispensed onto a film which is a target object, it is possible to observe the conditions of the film before and after dispensation or observe the time-varying film condition during the reaction.

This dispensing apparatus has an application in dispensation of reagents onto solid-phase materials such as a PVDF (polyvinylidene difluoride) film. Such a PVDF film includes spots spread by thin-layer chromatography and transferred thereto and, reagents are dispensed in order to color the spots. Such a solid-phase material may be nitrocellulose or nylon (registered trademark), as well as PVDF films.

Figure 4:
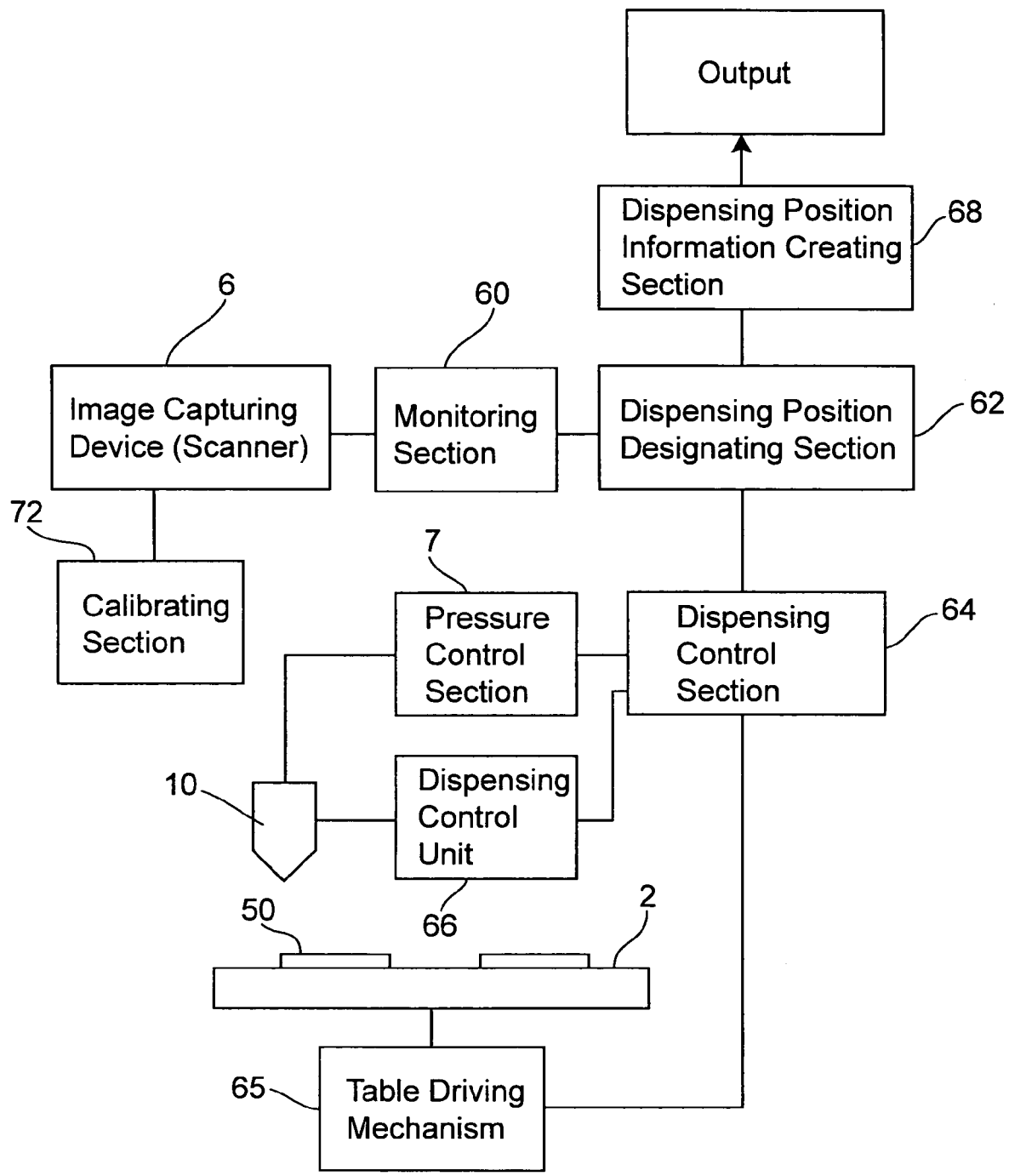
FIG. 4 is a block diagram illustrating the function of the present embodiment.

FIG. 4 is a block diagram illustrating the functions of the device of FIG. 1.

Reference numeral 60 denotes a monitoring section for displaying images captured by the image capturing device 6 such as a scanner. A dispensing position designating section 62 is for designating the dispensing positions on the target object 50 based on images of the target object 50 such as a membrane displayed on the monitoring section 60. A dispensing control section 64 is for positioning the target object and the dispensing device relative to each other so that the dispensing position on the target object designated by the dispensing position designating section 62 is beneath the dispensing device 10 and for controlling the dispensing operation of the dispensing device 10. When the dispensing device 10 includes a piezo device, the dispensing control section 64 causes a pressure control section 7 to adjust the pressure within the dispensing device 10 and also causes a dispensing control unit 66 to control the voltage application to the piezo device, in order to cause the piezo device to discharge liquid therefrom.

A dispensing position information creating section 68 is for creating dispensing position information about the dispensing positions on the target object 50 which are designated by the dispensing position designating section 62 and onto which the dispensing operation has been performed. The dispensing position information creating section 68 can output the created dispensing position information to the outside.

The target object 50 is provided with plural reference points "b" serving as positional references within the target object as illustrated in FIG. 2 and the image capturing device 6 is configured to capture images of the reference points "b" as well as images of the target object 50. Thus, the analysis position information creating section 68 can create the positions on the target object 50 designated by the analysis position designating section 62 based on the plural reference points "b". Even if the target object is removed and then mounted on the table 2 again, the dispensing device can be accurately positioned based on the reference points "b" by capturing images with the scanner 6. Furthermore, when the target object 50 is transferred to an analysis apparatus, etc., the analysis apparatus can be accurately positioned with respect to the dispensed positions on the target object 50 based on the reference points "b" and from the dispensing position information.

The table 2 for supporting the target object is moved within a plane by being driven by a table driving mechanism 65 and positioned at a predetermined position designated by the dispensing control section 64. The table 2 may be provided with plural reference base points "a" thereon and the image capturing device 6 may capture images of the base points "a" along with images of the target object 50. The analysis position information creating section 68 also may be configured to create the positions on the target object 50 based on the plural base points "a". This enables accurately determining dispensing position information within the target object 50 based on the base points "a".

The dispensing device 10 for dripping a sample or a reagent is configured to be detachable, and a calibrating section 72 for calibrating the dispensing position of the dispensing device 10 is provided. The calibrating section 72 detects the dispensing position based on images captured by the image capturing device 6 when liquid has been dispensed from the dispensing device 10 onto a predetermined position on the table 2 and calibrates the dispensing position based on the reference base point on the table which have been captured concurrently. For calibration, liquid is dispensed onto predetermined plural positions as illustrated by three points on a membrane 53 which colors when a reagent is dispensed thereon on the table 2 as illustrated in FIG. 2. Such calibration is performed each time the dispensing device is mounted thereon.

While in the aforementioned embodiments the present invention has been described with respect to cases where it is applied to a dispensing device, the position information to be determined is not limited to information of dispensing positions and the present invention can be also applied to cases where images of a membrane or a migration medium are captured with an image capturing device and information of detected positions such as spots in the images is created.

Hereinafter, an embodiment of a dispensing device according to a fifth aspect will be described.

Figure 5:
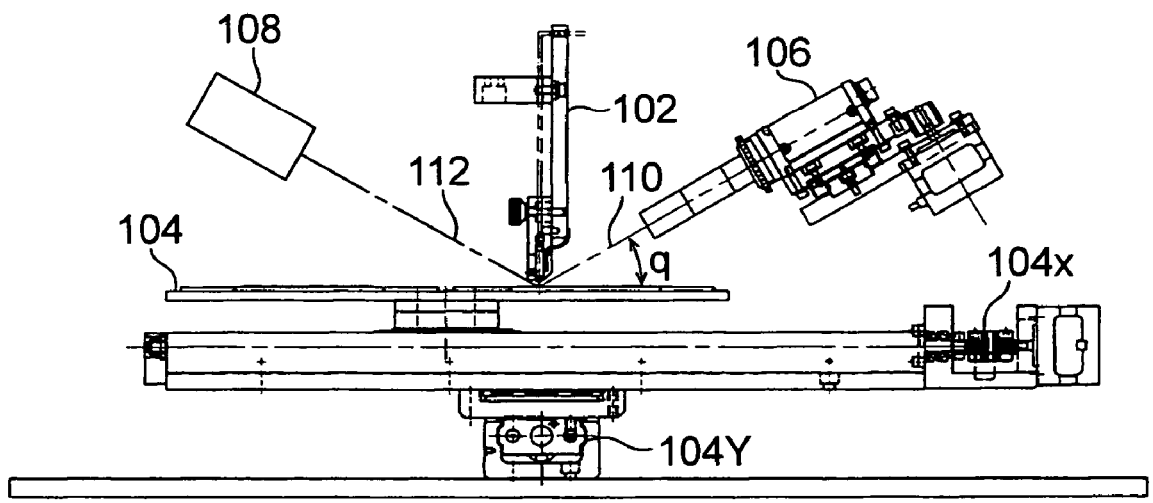
FIG. 5 is a front view illustrating an embodiment of a dispensing device according to a fifth aspect.

FIG. 5 illustrates an embodiment of the dispensing device according to the fifth aspect A dispensing mechanism 102 for dispensing a reagent (or a sample) includes a nozzle at its lower end for dripping a small amount of liquid. An X-Y table 104 which is a movable table is placed under the dispensing mechanism 102 and a target object onto which a reagent is to be dispensed is placed on the X-Y table 104. The X-Y table 104 includes a Y-driving mechanism 104Y for driving the target-object supporting surface in the vertical direction (Y direction) with respect to the paper plane in the figure and an X-driving mechanism 104X for driving the target-object supporting surface in the lateral direction (X direction), the X-driving mechanism 104X being mounted on the Y-driving mechanism 104Y. The target-object supporting surface of the X-Y table 104 is moved in the Y direction and the X direction within a horizontal plane by the Y-driving mechanism 104Y and the X-driving mechanism 104X to position the target object placed on the supporting surface beneath the nozzle of the dispensing mechanism 102.

An image capturing device 106 such as a CCD camera is mounted obliquely above the nozzle tip end of the dispensing mechanism 102 so that the light-receiving axis 110 of the image capturing device 106 is at an angle θ with respect to the horizontal direction. The image capturing device 106 is set to capture images of liquid drops formed at the nozzle tip end of the dispensing mechanism 102.

The position of the image capturing device 106 in a plane is within the range of the movement of the X-Y table 104. However, the mounting position of the image capturing device 106 is set above the X-Y table 104 in order to prevent contact between the X-Y table 104 and the image capturing device 106 even when the X-Y table 104 is moved within the range of movement There is an appropriate range of the angle θ between the light-receiving axis 110 of the image capturing device 106 and the horizontal plane. The θ is set to a value which can at least prevent interference of the image capturing device 106 with the X-Y table 104 and within a range which enables capturing an image of a liquid drop of a sample or a reagent formed at the tip end of the nozzle of the dispensing mechanism 102. An appropriate value of the angle θ is within the range of about 15 to 45 degrees.

A light source 108 is mounted at the position opposite the image capturing device 106 with respect to the nozzle tip end above the X-Y table 104, and the image capturing device 106 can capture the image using the transmitted light.

Figure 6:
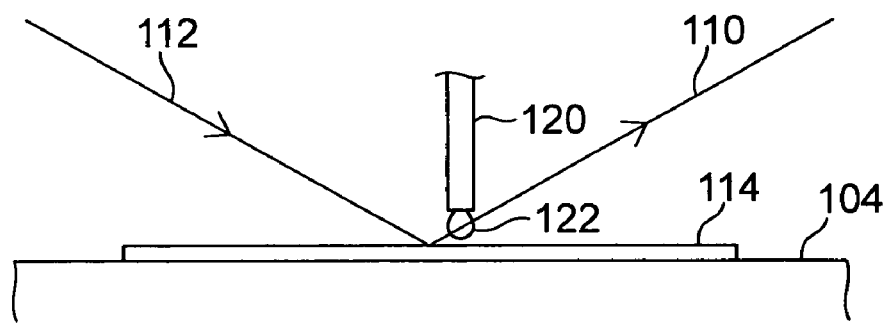
FIG. 6 is a schematic front view illustrating around the nozzle tip end according to the same embodiment.

As illustrated in FIG. 6, the relative positional relationship among the light source 108, the image capturing device 106, the nozzle 120 and the target object 114 is set so that light 112 emitted from the light source 8 is reflected at the surface of the target object 114 on the X-Y table 104, then passes through a liquid drop 122 formed at the tip end of the nozzle 120 of the dispensing mechanism 102 and then enters the image capturing device 106 along the light-receiving axis 110 of the image capturing device 106.

It is preferred that the depth of field of the image capturing device 106 is set so that the image capturing device 106 is focused on the liquid drop 122 at the nozzle tip end and on the surface of the target object 114 under it This enables capturing images of the liquid drop 122 at the nozzle tip end and the condition of the surface of the target object 114 and monitoring them concurrently.

This dispensing apparatus has an application in dispensation of reagents onto solid-phase materials such as a PVDF (polyvinylidene difluoride) film. Such a PVDF film includes spots spread by thin layer chromatography and transferred thereto, and reagents are dispensed in order to color the spots. Such solid-phase material may be also nitrocellulose or nylon (registered trademark), as well as PVFD films.

A reagent or sample is repeatedly dispensed to a plurality of dispensing positions from the nozzle tip end by moving the X-Y table 4. During this, in monitoring the shapes of liquid drops dripped from the nozzle tip end, the image capturing device 106 can capture images at fixed timing since the start of dripping of each liquid drop 122 from the nozzle 120, thus enabling treating the images of liquid drops as images captured with the same timing.

As a method for realizing such image capturing, a strobe light may be employed as the light source 108 and the image capturing device 106 is set to continuously capture images, wherein the strobe light is tuned on after a constant time has elapsed since the start of dripping from the nozzle 120. This facilitates capturing images of a plurality of liquid drops with the same timing and monitoring the shapes of the liquid drops. Such monitoring of liquid-drop shapes can be utilized in controlling the voltage applied to a piezo device or in controlling the opening and closing of a valve in dispensing mechanisms for dispensing samples or reagents so that the shapes of liquid drops which are repeatedly discharged are maintained constant.

The light source 108 is not limited to a strobe light and may be any light sources which continuously emit light and, in such cases, the image capturing device 106 is controlled to capture images with a constant timing since the start of dripping of each liquid drop 122.

Figure 7:
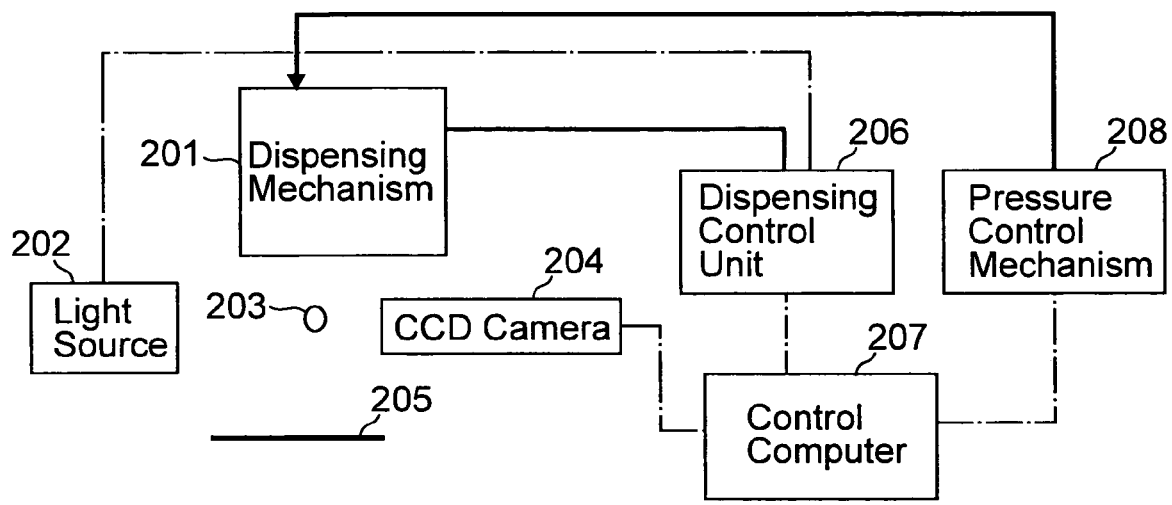
FIG. 7 is a block diagram schematically illustrating an embodiment according to a sixth aspect.
Figure 8:
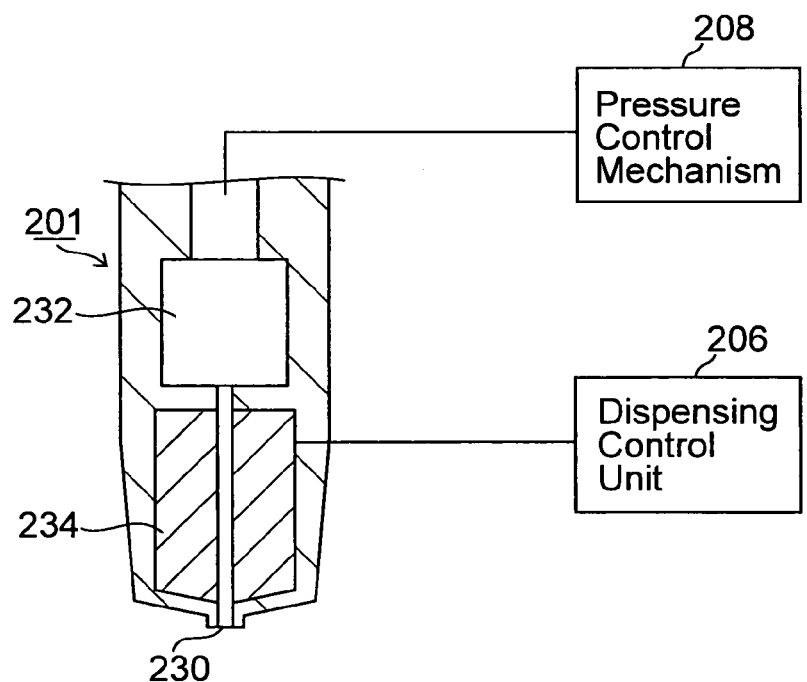
FIG. 8 is a cross sectional view schematically illustrating an exemplary piezo chip according to the same embodiment.

FIG. 7 schematically illustrates a dispensing apparatus according to an embodiment of a sixth aspect Reference numeral 201 denotes a dispensing mechanism provided with a piezo chip, which is one as will be illustrated in FIG. 8. Reference numeral 203 denotes a liquid drop discharged from the piezo chip, which will be dispensed onto a target 205 such as a container or a plate retained beneath the dispensing mechanism 201. A CCD camera 204, as an image capturing device, is placed for capturing images of the discharging portion at the tip end of the dispensing mechanism 201 and monitoring the discharging portion. The CCD camera 204 can photograph the discharging portion and drops 203 discharged therefrom, concurrently. The image capturing device is not limited to a CCD camera, and other cameras may be used.

The CCD camera 204 photographs the tip end of the dispensing mechanism 1 along a horizontal direction. Although the tip end can be photographed at an angle from above with respect to the horizontal direction, it is preferable that the tip end of the discharging portion is photographed along the horizontal direction in order to accurately monitor the tip end of the discharging portion.

In the present embodiment, in order to enable more accurately capturing images of the tip end of the dispensing mechanism 201, a light source 2 is placed at the position opposite to the CCD camera 204 with respect to the tip end of the dispensing mechanism 1 along the light axis of the CCD camera 204 for enabling photographing using the transmitted light Although the light source 202 may be a light source which continuously emits light, a strobe light is employed as the light source 204 in the present embodiment In the case of using a strobe light, the strobe light may be set to emit light in synchronization with the timing of discharging of the liquid drops 203 from the dispensing mechanism 201 and, in such a case, even when the camera 204 is continuously operated, the camera 204 can capture clear images only at the instant when the strobe light 202 emits light Since the clear images are images of sequentially discharged liquid drops 203 captured with the same timing, information can be obtained as though it were static image. This is advantageous in monitoring the conditions of liquid drops 203.

Reference numeral 206 denotes a dispensing control unit which applies a voltage to the piezo device of the dispensing mechanism 201 for causing it to discharge liquid. Furthermore, the timing of light emission of the strobe light 202 is controlled by the dispensing control unit 206 so that it is in synchronization with the timing of the voltage application to the piezo device of the dispensing mechanism 201 and the strobe light 202 emits light after a constant time has elapsed since the discharging of each liquid drop from the dispensing mechanism 201.

Reference numeral 208 denotes a pressure control mechanism for maintaining the to-be-discharged liquid, such as a sample or reagent, which is charged in a reservoir, at a constant pressure, wherein the reservoir is a space in the dispensing mechanism 201 for enabling charging liquid therein. In the present invention, the pressure control mechanism 208 is also used in adjusting the liquid level at the tip end of the discharging portion prior to the start of the discharging operation.

Reference numeral 207 denotes a control computer which controls the dispensing control unit 206 for controlling the dispensing operation and includes a storing device for storing images captured by the CCD camera 204. The control computer 207 also compares an image of the discharging portion captured and stored in the storing device before charging liquid in the reservoir of the piezo chip in the dispensing mechanism 201 with images of the tip end captured after charging liquid in the reservoir and controls the pressure control mechanism 208 so that, when liquid appears from the discharging portion, the liquid is retracted until there is no difference between these images captured after liquid charging and the image captured before liquid charging, thus realizing the function of a control device for controlling the pressure control mechanism 208.

FIG. 8 schematically illustrates an examplery piezo chip in the dispensing mechanism 201.

The piezo chip includes a flow path extending from the reservoir 232 to the hole of the discharging portion 230 and discharges liquid from the discharging portion 230 when a driving section 234 including a piezo device pushes the liquid in the reservoir 232 or the flow path. The dispensing control unit 6 controls the driving of the piezo device. The reservoir 232 is connected to the pressure control mechanism 208 in order to maintain a constant pressure even when the sample or reagent in the reservoir 232 has been reduced.

The parameters for controlling the driving of the piezo device by the dispensing control unit 206 include all or at least one of the amplitude of the voltage applied on the piezo device, the rising time of the applied voltage, the applying time period and the descending time of the applied voltage.

Figure 9:
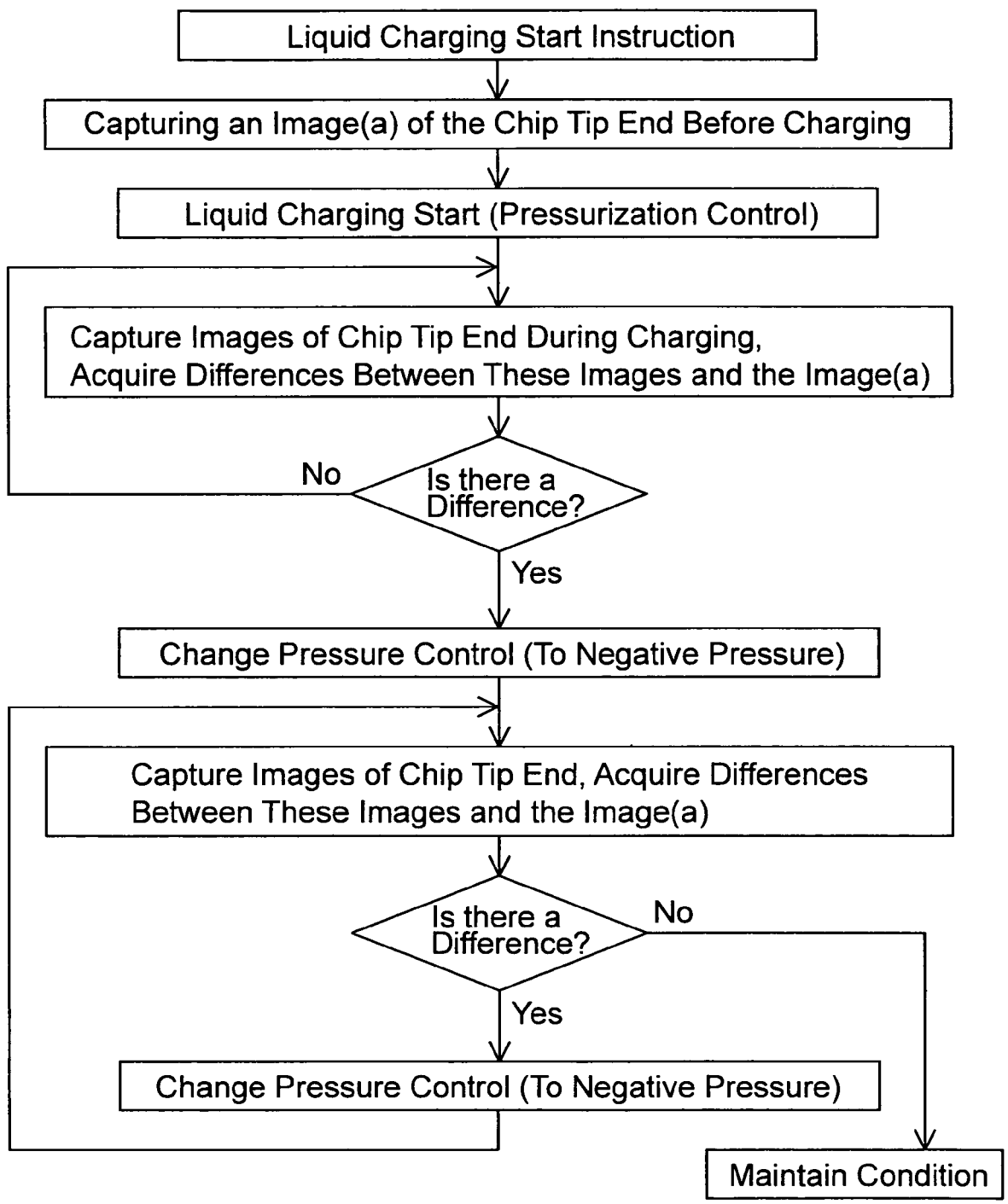
FIG. 9 is a flow chart illustrating the operation according to the same embodiment.

With reference to FIG. 9, there will be described the operation for adjusting the liquid level at the discharging portion tip end prior to the start of the dispensing operation according to the present embodiment While in the present embodiment there will be described an automated adjustment using the control computer 7, this operation may be manually achieved by referring to images of the discharging portion tip end.

Prior to the start of dispensation, a solution is charged at first Observations of the tip end of the piezo chip can be performed by capturing images by the CCD camera 204.

When charging of solution into the piezo chip is ordered through the control computer 7, the control computer 207 causes the CCD camera 204 to capture an image of the piezo chip tip end before charging therein and then stores the image. This image will be referred to as an image (a), hereinafter.

Then, the control computer 207 controls the pressure control mechanism 208 to pressurize the solution and to push it towards the piezo chip tip end. During this, the control computer 7 causes the CCD camera 204 to capture images of the piezo chip tip end at regular time intervals and determines the differences between these images and the image (a) captured before the charging. If there is a difference, this means that an excess solution has been extruded from the piezo chip tip end. Therefore, when such a condition is detected, the pressure control is changed to a feedback pressure control. During this, the control computer 207 uses the CCD camera 204 to capture images of the piezo chip tip end at regular time intervals and determines the differences between the images and the image (a) captured before the charging. The feedback pressure control is performed at regular time intervals and, when it is detected, from the differences in the images, that there is no excess amount of liquid, the feedback is stopped and the condition is retained.

Figure 10:
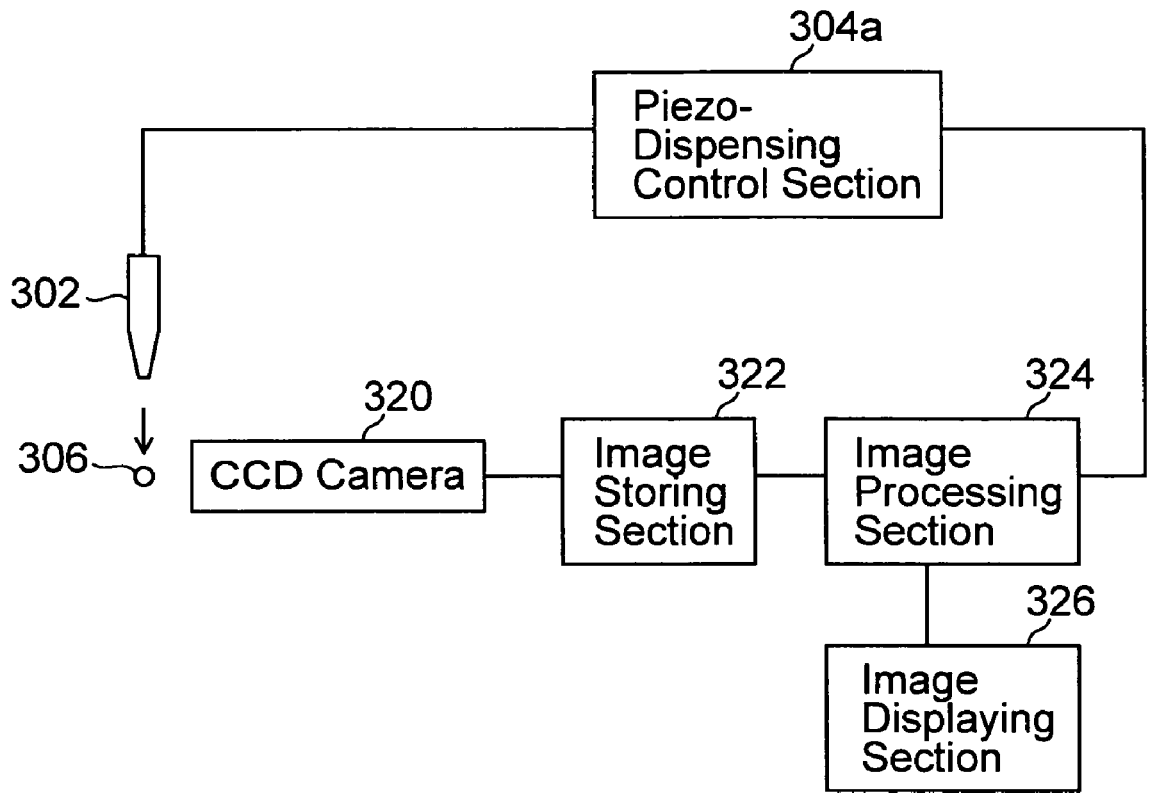
FIG. 10 is a block diagram schematically illustrating an apparatus utilizing the method of an embodiment of a seventh aspect.

FIG. 10 schematically illustrates an apparatus utilizing the method of an embodiment of a seventh aspect, wherein a case is illustrated where the sizes of liquid drops are automatically determined and also automatically controlled to be constant, utilizing a piezo-type dispensing device.

In order to capture images of liquid drops 306 discharged from the piezo chip 302, a CCD camera 320 is provided, as an image capturing device, which is oriented to liquid drops 6 discharged from the piezo chip 302. Reference numeral 322 denotes an image storing section for storing images captured by the CCD camera 320. The CCD camera 320 captures images in or out of synchronization with the timing of discharging of liquid drops 6.

Reference numeral 324 denotes an image processing section which applies image processing such as binarization or outline extraction to the images stored in the image storing section 322, determines the diameters or the radii of liquid drops and calculates the amount of dispensed liquid. When the CCD camera 320 captures images in synchronization with the discharging of liquid drops, the images of liquid drops to be processed by the image processing section 324 are those at the same timing from the discharging of the respective liquid drops. When the CCD camera 320 captures images out of synchronization therewith, the CCD camera 320 captures a plurality of images of a single image in time sequence and, out of the images, the images of the liquid drops passing the same position are selected and subjected to the image processing in the image processing section 324.

Reference numeral 326 denotes an image processing section for displaying images of liquid drops which have been subjected to the image processing. Furthermore, the amount of dispensed liquid determined from the image processing at the image processing section 324 is supplied to a piezo dispensing control section 304a. The piezo dispensing control section 304a controls the driving of the piezo chip 302 so that the amount of liquid (the size of liquid drop 6) which will be subsequently discharged from it will become equal to a predetermined set value.

Figure 11:
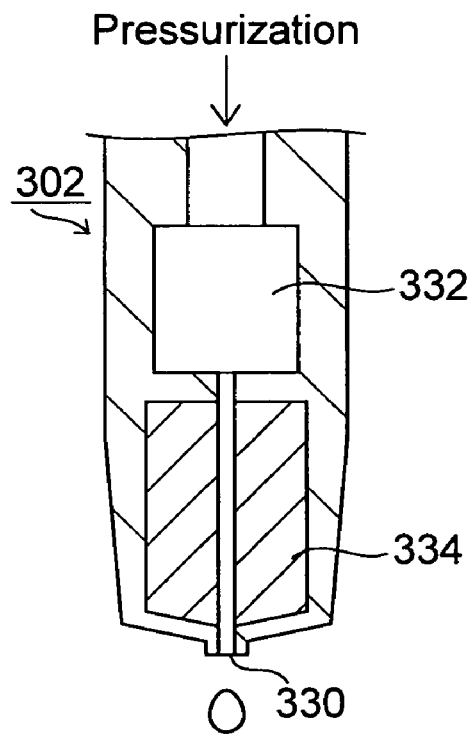
FIG. 11 is a cross sectional view schematically illustrating an exemplary piezo chip in the same apparatus.
Figure 12:
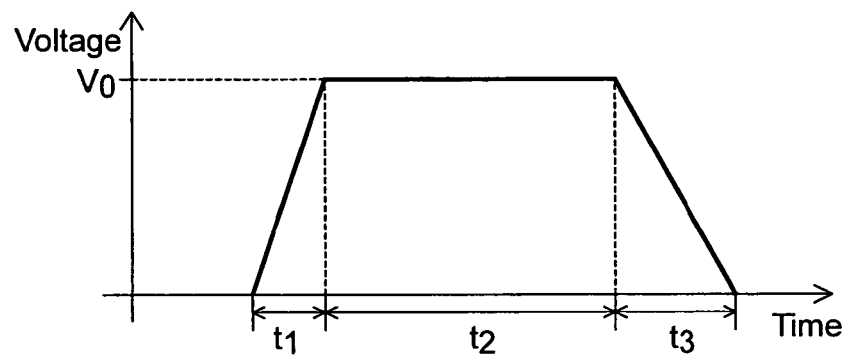
FIG. 12 is a waveform diagram illustrating a control parameter according to the same embodiment.

As illustrated in FIG. 11, for example, the piezo chip 302 discharges liquid from the discharging portion 330 when a driving section 334 including a piezo device pushes the liquid reservoir 332 communicated to the hole of the discharging portion 330 at the tip end. The liquid reservoir 332 is connected to a pressurizing section (not shown) in order to maintain a constant pressure even when the sample or reagent in the liquid reservoir 332 has been reduced.

The parameters for controlling the driving of the piezo chip 2 by the piezo dispensing control section 304a include all or at least one of the amplitude of the voltage applied on the piezo device $V_0$, the rising time of the applied voltage $t_1$, the voltage applying time period $t_2$ and the descending time of the applied voltage $t_3$.

Figure 13:
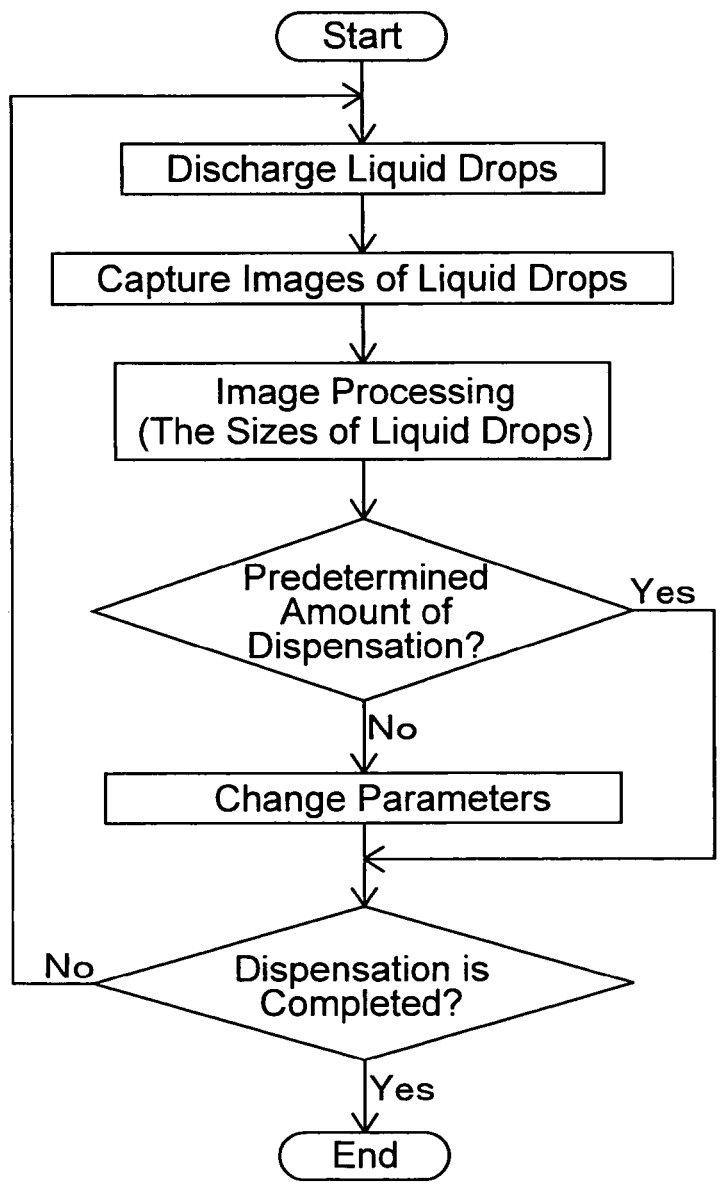
FIG. 13 is a flow chart illustrating the operation according to the same embodiment.

FIG. 13 comprehensively illustrates the operations according to the present embodiment.

The driving of the piezo chip 302 is controlled with predetermined piezo chip control parameters to discharge liquid drops 6. The CCD camera 320 captures images of liquid drops 306 in or out of synchronization with the discharging of liquid drops and stores these images in the image storing section 322. The image processing section 324 applies image processing such as binarization or outline extraction to the images stored in the image storing section 322, determines the diameters or the radii of the liquid drops and calculates the amounts of dispensed liquid. When the amount of dispensed liquid is a predetermined value, the piezo dispensing control section 304a does not change the piezo chip control parameters and repeatedly drives the piezo chip 302. However, when the amount of dispensed liquid is not the predetermined value, the piezo dispensing control section 304a changes the piezo chip control parameters and controls the driving of the piezo chip 302 so that the amount of liquid which will be subsequently discharged therefrom will become equal to the predetermined value.

Figure 14:
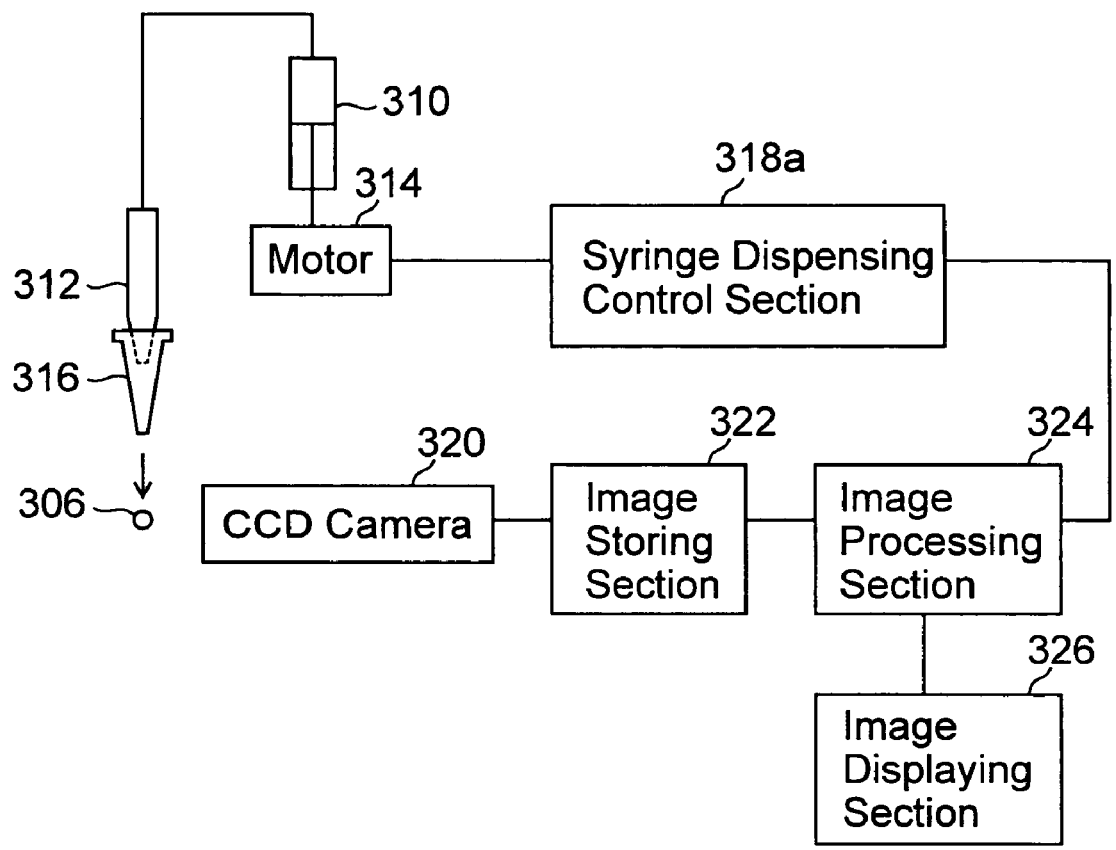
FIG. 14 is a block diagram schematically illustrating an apparatus utilizing a method of another embodiment of the same aspect.

FIG. 14 schematically illustrates an apparatus utilizing a method according to another embodiment, wherein a case is illustrated where the sizes of liquid drops are automatically determined and also automatically controlled to be constant, utilizing a dispensing device employing a syringe pump.

A syringe dispensing control section 318a controls and drives a motor 14 for operating the syringe pump 310 to cause a probe 312 connected to the syringe pump 310 to discharge liquid drops 6. A disposable chip 316 is provided at the tip end of the probe 312.

The CCD camera 320 for capturing images of liquid drops 306, the image storing section 322, the image processing section 324 and the image displaying section 326 are similar to those illustrated in FIG. 10.

The syringe dispensing control section 318a acquires data regarding sizes of liquid drops such as the diameters or the radii of the liquid drops 306 from the image processing section 324 and controls the driving of the motor 314 so that the sizes of liquid drops 306 which will be subsequently discharged therefrom will become equal to the predetermined set value.

The parameters for controlling the driving of the motor 314 by the syringe dispensing control section 318a include all or at least one of the stroke, the speed and the acceleration of the plunger.

Figure 15:
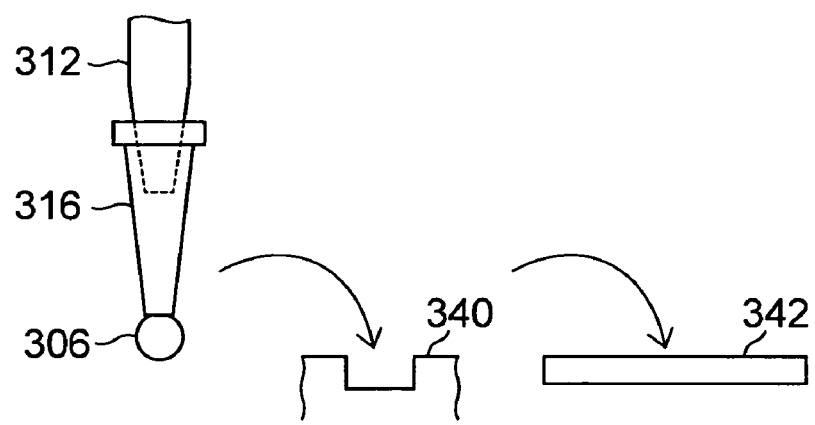
FIG. 15 is a front view of the probe tip end illustrating the dispensing system according to the same embodiment.
Figure 16:
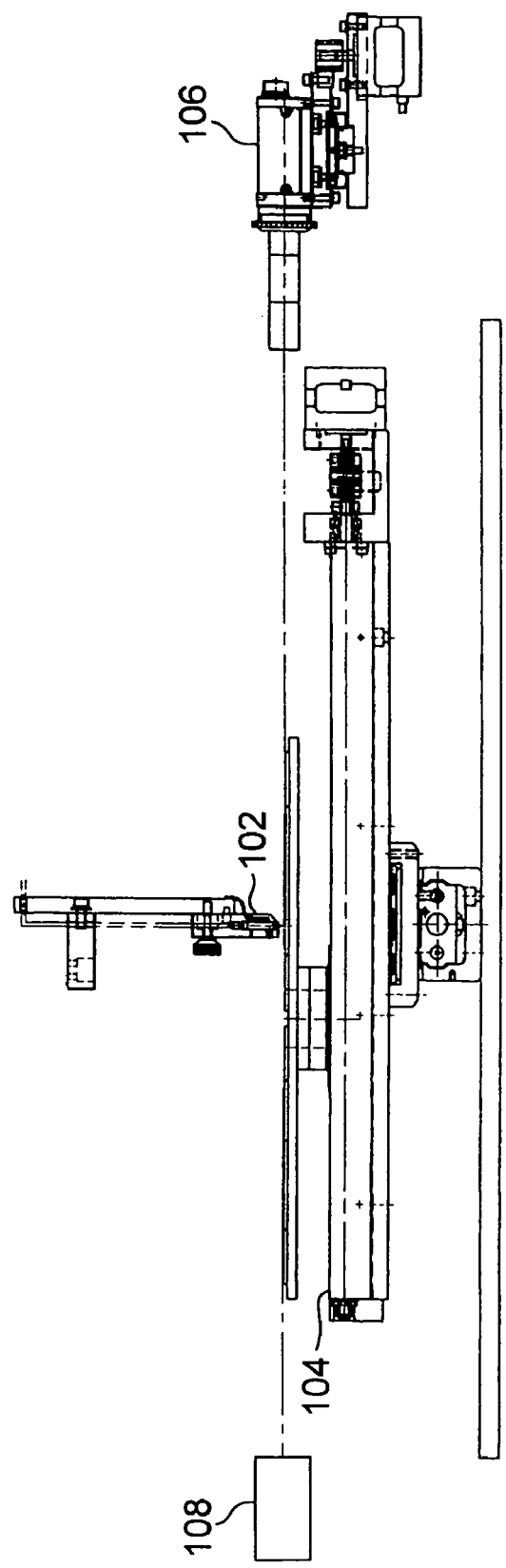
FIG. 16 is a front view illustrating a conventional dispensing apparatus corresponding to the dispensing apparatus according to the fifth aspect.
Figure 17:
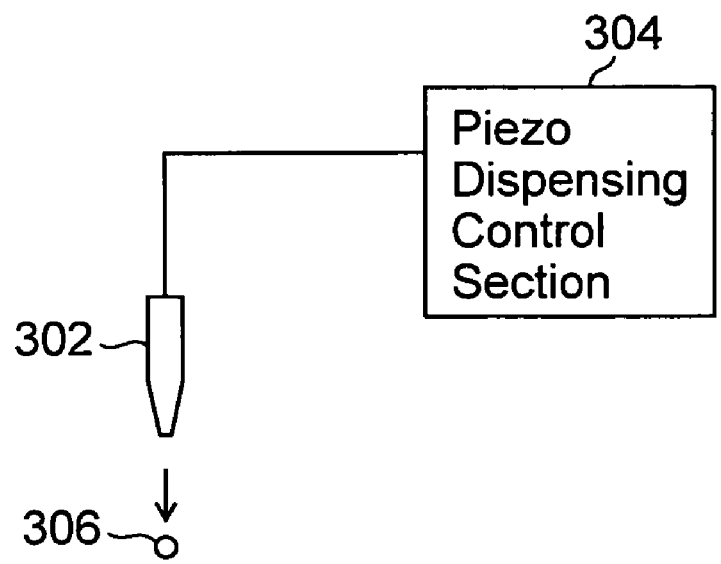
FIG. 17 is a block diagram schematically illustrating a conventional piezo-type dispensing apparatus.
Figure 18:
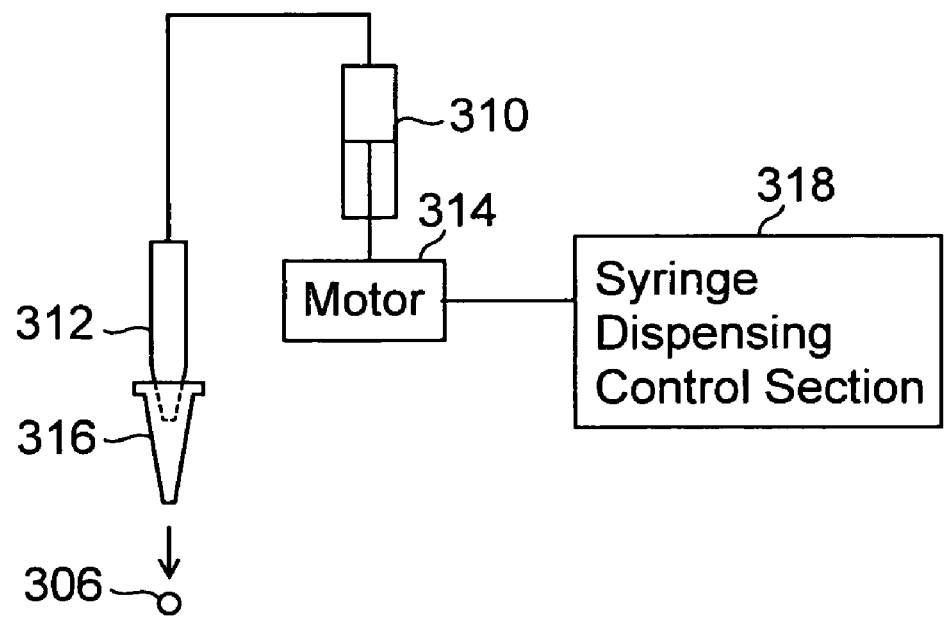
FIG. 18 is a block diagram schematically illustrating a conventional syringe-type dispensing apparatus.

As illustrated in FIG. 15, when liquid drops 306 on the order of a few hundred nanoliters to a few microliters are dispensed onto a container 340 or a plate 342 by the syringe system, ball-shaped liquid drops 306 are hung from the tip end of the disposable chip 316 (the tip end of the probe 312, in the case of using no disposable chip 316). Thus, the CCD camera 320 captures images of liquid drops 6 in this state and the image processing section 322 applies image processing such as binarization or outline extraction to the images, determines the diameters or the radii of the liquid drops and calculates the amounts of dispensed liquid. When the determined amount of liquid which corresponds to the size of a liquid drop 306 is greater than a target amount, the syringe dispensing control section 318a puts back the plunger in controlling the driving of the motor 14. When the determined amount of liquid is smaller than the target amount, the syringe dispensing control section 318a pushes the plunger to adjust the amount of dispensed liquid in real time. Thus, liquid drops 306 at the probe or the disposable chip are dispensed into the container 340 or the plate 342.

When the present invention is applied to the syringe-pump dispensing system, the present invention can be similarly applied to cases where the chip 316 is a disposable chip containing a filter or a carrier therein.

INDUSTRIAL APPLICABILITY

The dispensing apparatuses according to the present invention can be utilized as a method and a device for dispensing a reagent, etc., onto a membrane, in order to form samples for mass spectrometry from materials spread and solidified on the membrane.

What is claimed is:

1. A liquid dispensing apparatus comprising:
a dispensing mechanism including a plurality of dispensing devices for dripping a sample or a reagent;
an image capturing device for capturing the downward area image;
a movable table capable of supporting, on its upper surface, a target object onto which the sample or reagent is to be dispensed and being moved on a horizontal plane surface for positioning the target object at least at a dispensing position beneath the dispensing device and at an image capturing position beneath the image capturing device;
a monitoring section for displaying the image captured by the image capturing device;
a dispensing position designating section for designating the dispensing position on the target object based on the image of the target object displayed on the monitoring section;
a dispensing control section for positioning the target object and the dispensing device relative to each other so that the dispensing position on the target object designated by the dispensing position designating section is placed beneath the dispensing device, which performs the dispensing operation, of the dispensing mechanism and for controlling the dispensing operation of the dispensing mechanism;
the image capturing device for photographing the tip end of the dispensing device; and
a moving mechanism for moving the image capturing device in association with the switching of the dispensing device performing the dispensing operation so that the image capturing device is capable of photographing the tip end of the dispensing device performing the dispensing operation.

2. A liquid dispensing apparatus according to claim 1, further comprising a dispensing position information creating section for creating dispensing position information about the dispensing position on the target object which is designated by the dispensing position designating section and for which the dispensing operation has been performed.

3. A liquid dispensing apparatus according to claim 2, wherein the dispensing position information creating section is capable of outputting the created dispensing position information to the outside.

4. A liquid dispensing apparatus according to claim 2, wherein the dispensing position designating section designates the dispensing position on the image of the target object displayed on the monitoring section.

5. A liquid dispensing apparatus according to claim 1, wherein the dispensing position information creating section is capable of outputting the created dispensing position information to the outside.

6. A liquid dispensing apparatus according to claim 5, wherein the dispensing position designating section designates the dispensing position on the image of the target object displayed on the monitoring section.

7. A liquid dispensing apparatus according to claim 1, wherein the dispensing position designating section designates the dispensing position on the image of the target object displayed on the monitoring section.

8. A dispensing apparatus comprising:
a dispensing mechanism including a detachable dispensing device for dripping a sample or reagent;
an image capturing device for capturing downward area image;
a movable table capable of supporting, on its upper surface, a target object onto which the sample or reagent is to be dispensed and being moved on a horizontal plane surface for positioning the target object at least at a dispensing position beneath the dispensing device and at an image capturing position beneath the image capturing device; and
a calibrating section which, after liquid is dispensed onto a predetermined position on the movable table by the dispensing mechanism, detects the dispensing position based on the image captured by the image capturing device and calibrates the dispensing position based on base points serving as references on the movable table, the base points being captured concurrently with the image, wherein the dispensing device has a discharging port at its lower end, and wherein the dispensing mechanism further comprising:

a dispensing device retaining portion fixed to a main body of the liquid dispensing apparatus, the retaining portion arranging the dispensing device with the discharging port facing downwardly;

dispensation liquid container arranged on the dispensing device retained by the retaining portion to communicate to the dispensing device;

an air-introducing head arranged on the dispensation liquid container for communicating to the dispensation liquid container to adjust an inner pressure of the dispensation liquid container; and an arm mechanism including an arm and a lock, the arm being supported rotatably at its base end on the main body to mount the air-introducing head detachably, the lock being capable of fixing the arm to the main body so that the air-introducing head is mounted on the dispensing device retained by the retaining portion through the dispensation liquid container and capable of releasing the fixing.

9. A liquid dispensing apparatus according to claim 8, wherein the dispensing mechanism includes a plurality of dispensing devices and the calibrating section performs the calibration for the respective dispensing devices.

10. A dispensing apparatus comprising:

a dispensing unit including a piezo chip having a downward opening portion at its discharging portion, the piezo chip being configured to discharge liquid from the discharging portion when liquid charged in a space communicated to the discharging portion is pushed by a driving section including a piezo device, a pressure control mechanism for adjusting the pressure of the liquid charged in the space;

an image capturing device for capturing an image of the discharging portion;

a storing device for storing the image captured by the image capturing device; and a control device which compares the image of the discharging portion captured before charging liquid in the space and stored in the storing device with images captured after charging liquid in the space and controls the pressure control mechanism so that, when liquid exits from the discharging portion, the liquid is retracted until the differences between the images and the image captured before charging liquid is cancelled.

11. A dispensing apparatus according to claim 10, wherein the image capturing device is installed so that it captures the image of the discharging portion along a horizontal direction.

* * * * *